United States Patent
Nishikawa et al.

(10) Patent No.: US 12,256,767 B2
(45) Date of Patent: *Mar. 25, 2025

(54) GARDENIA BLUE PIGMENT AND METHOD FOR PRODUCING THE SAME

(71) Applicant: GLICO NUTRITION CO., LTD., Osaka (JP)

(72) Inventors: Masahiro Nishikawa, Osaka (JP); Junya Yamashita, Osaka (JP); Kaori Miura, Osaka (JP); Kenichi Fujimori, Osaka (JP)

(73) Assignee: GLICO NUTRITION CO., LTD., Osaka (JP)

( * ) Notice: Subject to any disclaimer, the term of this patent is extended or adjusted under 35 U.S.C. 154(b) by 488 days.

This patent is subject to a terminal disclaimer.

(21) Appl. No.: 17/603,675

(22) PCT Filed: Apr. 6, 2020

(86) PCT No.: PCT/JP2020/015493
§ 371 (c)(1),
(2) Date: Oct. 14, 2021

(87) PCT Pub. No.: WO2020/213447
PCT Pub. Date: Oct. 22, 2020

(65) Prior Publication Data
US 2022/0232864 A1    Jul. 28, 2022

(30) Foreign Application Priority Data
Apr. 16, 2019 (JP) .................... 2019-078125

(51) Int. Cl.
*A23L 5/43* (2016.01)
*C07D 311/94* (2006.01)

(52) U.S. Cl.
CPC .............. *A23L 5/43* (2016.08); *C07D 311/94* (2013.01); *A23V 2002/00* (2013.01)

(58) Field of Classification Search
CPC ....................................................... A23L 5/43
See application file for complete search history.

(56) References Cited

U.S. PATENT DOCUMENTS

| | | |
|---|---|---|
| 2018/0258286 A1 | 9/2018 | Kasai |
| 2021/0292567 A1 | 9/2021 | Horn et al. |
| 2022/0195197 A1 | 6/2022 | Yamashita et al. |

FOREIGN PATENT DOCUMENTS

| | | |
|---|---|---|
| JP | 52053934 A | 4/1977 |
| JP | 56092792 A | 7/1981 |
| JP | 1179690 A | 7/1989 |
| JP | 07111896 A | 5/1995 |
| JP | 2015091946 A | 5/2015 |
| JP | 2017063650 A | 4/2017 |
| JP | 2018536730 A | 12/2018 |
| JP | 7323322 B2 | 8/2023 |
| WO | 03029358 A1 | 4/2003 |
| WO | 2006082922 A1 | 8/2006 |
| WO | 2016045100 A1 | 3/2016 |
| WO | 2017057187 A1 | 4/2017 |
| WO | 2017156744 A1 | 9/2017 |
| WO | 2018029338 A1 | 2/2018 |

OTHER PUBLICATIONS

English Translation of ISR of corresponding Application No. PCT/JP2020/015493 mailed Jul. 7, 2020.
Xu, You-zhi, et al., "Study on Preparation and Stability of High Color Value Gardenia Blue", Modern Food Science and Technology, 2011, vol. 27, No. 4, pp. 440-443, Table 1.
Office Action for corresponding Japanese Application No. 2021-514883 Issued Mar. 12, 2024.
Office Action for corresponding Japanese Application No. 2022-545226 dated Jul. 9, 2024.

*Primary Examiner* — Katherine D Leblanc
(74) *Attorney, Agent, or Firm* — Renner, Otto, Boisselle & Sklar, LLP

(57) ABSTRACT

An object of the present invention is to provide a gardenia blue pigment that exhibits a vivid blue tone that is bright and has reduced redness, and a method for producing the gardenia blue pigment. A gardenia blue pigment that exhibits a vivid blue tone that is bright and has reduced redness is obtained by carrying out the following first and second steps: the first step of reacting at least one peptide selected from the group consisting of soy peptide, sesame peptide, and rice peptide with genipin in a solvent without the supply of a gas containing oxygen; and the second step of treating the reaction solution obtained in the first step with the supply of a gas containing oxygen.

5 Claims, No Drawings

GARDENIA BLUE PIGMENT AND METHOD FOR PRODUCING THE SAME

This application is a national phase of International Application No. PCT/JP2020/015493 filed 6 Apr. 2020, which claims priority to Japan Application No. 2019-078125 filed 16 Apr. 2019, the entireties of which are hereby incorporated by reference.

TECHNICAL FIELD

The present invention relates to a gardenia blue pigment that exhibits a vivid blue tone that is bright and has reduced redness. The present invention also relates to a method for producing the gardenia blue pigment.

BACKGROUND ART

Blue colorants for use in food products and the like are conventionally known, such as Food Blue No. 1 (disodium 2-(bis{4-[N-ethyl-N-(3-sulfonatophenylmethyl)amino]phenyl}methyliumyl)benzenesulfonate), spirulina pigment, and gardenia blue pigment. Food Blue No. 1 and spirulina pigment are pigments that exhibit a blue color that is bright, low in redness and high in yellowness, and brilliant, and are characterized by having a vivid blue tone. However, with growing consumer awareness of food safety, the use of Food Blue No. 1, which is a synthetic colorant, tends to be avoided. Spirulina pigment, which is a natural pigment, has a drawback in that it easily fades with heat, and is expensive. On the other hand, gardenia blue pigment is a natural pigment, which has stability to heat, and overcomes the drawbacks of Food Blue No. 1 and spirulina pigment, and is widely used in the food industry, for example.

Gardenia blue pigment is produced by the action of a β-glucosidase and a primary amino group-containing compound on an iridoid glycoside obtained from the fruit of *Gardenia jasminoides* Ellis of Rubiaceae under aerobic conditions. However, gardenia blue pigment obtained by this process is not satisfactory in terms of color tone because it is not sufficiently bright, and is reddish.

Thus, various studies have heretofore been made on techniques that can improve the color tone of gardenia blue pigment.

For example, Patent Literature 1 discloses subjecting an iridoid glycoside derived from the fruit of *Gardenia jasminoides* Ellis of Rubiaceae to a β-glucosidase treatment in the presence of a casein hydrolysate treated with a proline-specific endoprotease, thereby obtaining a gardenia blue pigment having a bright blue tone with reduced red-purpleness.

Patent Literatures 2 and 3 disclose carrying out the steps of a) treating geniposide with a glucosidase to obtain a hydrolysate; b) extracting the hydrolysate obtained in step a) with a solvent to obtain a product containing genipin; and c) reacting the product obtained in step b) with an aqueous solution containing an amino acid and/or a salt thereof to produce a gardenia blue pigment, thereby obtaining a gardenia blue pigment having a bright blue tone.

Patent Literature 4 discloses carrying out the step of blending a polyphenol into a gardenia blue pigment prepared by subjecting an iridoid glycoside extracted from the fruit of *Gardenia jasminoides* Ellis of Rubiaceae to a β-glucosidase treatment in the presence of a protein hydrolysate, or subjecting an iridoid glycoside extracted from the fruit of *Gardenia jasminoides* Ellis of Rubiaceae to a β-glucosidase treatment in the presence of a protein hydrolysate and a polyphenol, thereby obtaining a gardenia blue pigment having a bright blue tone with reduced red-purpleness.

Patent Literature 5 discloses that, in the production of a gardenia blue pigment by allowing an aglycone of an iridoid glycoside and a taurine-containing substance to coexist under aerobic conditions, a polyphenol compound is added during or after the production, thereby obtaining a gardenia blue pigment with a bright color tone.

However, the gardenia blue pigments obtained using the techniques of Patent Literatures 1 to 5 are still reddish, and are still not satisfactory in terms of color tone, and these techniques cannot produce a gardenia blue pigment with a blue tone that is bright and has reduced redness to a degree comparable to Food Blue No. 1 or spirulina pigment.

CITATION LIST

Patent Literatures

Patent Literature 1: WO 2006/82922
Patent Literature 2: WO 2016/45100
Patent Literature 3: WO 2017/156744
Patent Literature 4: WO 2003/29358
Patent Literature 5: JP 7-111896 A

SUMMARY OF INVENTION

Technical Problem

It is an object of the present invention to provide a gardenia blue pigment that exhibits a vivid blue tone that is bright and has reduced redness, and a method for producing the gardenia blue pigment.

Solution to Problem

As a result of extensive research to solve the aforementioned problem, the present inventors have found that a gardenia blue pigment that exhibits a vivid blue tone that is bright and has reduced redness can be obtained by carrying out the first step of reacting at least one peptide selected from the group consisting of soy peptide, sesame peptide, and rice peptide with genipin in a solvent without the supply of a gas containing oxygen; and the second step of treating the reaction solution obtained in the first step with the supply of a gas containing oxygen. The inventors have also found that the gardenia blue pigment obtained by carrying out the first and second steps, when prepared as a solution with a color value $E^{10\%}_{1\ cm}$ of 0.1 by diluting with water, has an L* value of 66 or more and an a* value of −24 or less in the Lab color space, and exhibits a color tone similar to Food Blue No. 1. Furthermore, the inventors have found that when the first and second steps are carried out using rice peptide as the peptide to be added, the obtained gardenia blue pigment not only exhibits a vivid blue tone that is bright and has reduced redness, but can also stably maintain the color tone even after heating under acidic conditions. The present invention has been completed by conducting further research based on these findings.

In summary, the present invention provides the aspects of the invention as set forth below:

Item 1. A gardenia blue pigment, wherein, when prepared as a solution with a color value $E^{10\%}_{1\ cm}$ of 0.1 by diluting with water, the gardenia blue pigment has an L* value of 66 or more and an a* value of −24 or less in the Lab color space.

Item 2. The gardenia blue pigment according to item 1, wherein, when prepared as a solution with a color value $E^{10\%}_{1\ cm}$ of 0.1 by diluting with water, the gardenia blue pigment has a b* value of −30 or more in the Lab color space.

Item 3. The gardenia blue pigment according to item 1 or 2, wherein when the gardenia blue pigment is subjected to operations as set forth in (1) to (3) below, a color difference $\Delta E^*_{ab}$ between solution A heat-treated at 90° C. for 15 minutes and solution B not heat-treated is 3.5 or less, and solution A heat-treated at 90° C. for 15 minutes has an L* value of 64 or more, an a* value of −14 or less, and a b* value of −31 or more:

<Operation Conditions>

(1) Preparation the gardenia blue pigment is diluted with 0.1 M citrate buffer at pH 2.5 to prepare solution A with a color value $E^{10\%}_{1\ cm}$ of 0.1; separately, the gardenia blue pigment is diluted with 0.1 M citrate buffer at pH 6.0 to prepare solution B with a color value $E^{10\%}_{1\ cm}$ of 0.1;

(2) Heat-Treatment of the Solutions solution A is heat-treated at 90° C. for 15 minutes; solution B is not heat-treated;

(3) Measurement of Color Tone for solution A heat-treated at 90° C. for 15 minutes and solution B not heat-treated, the L value, the a* value, and the b* value in the Lab color space are measured.

Item 4. The gardenia blue pigment according to any one of items 1 to 3, wherein a maximum absorption wavelength is present in a range of 604 nm or more.

Item 5. A food or beverage product colored with the gardenia blue pigment according to any one of items 1 to 4.

Item 6. A method for producing a gardenia blue pigment, comprising the following first and second steps:

first step: reacting at least one peptide selected from the group consisting of soy peptide, sesame peptide, and rice peptide with genipin in a solvent without the supply of a gas containing oxygen; and second step: treating the reaction solution obtained in the first step with the supply of a gas containing oxygen.

Item 7. The method according to item 6, wherein the peptide contains 45% or more of peptides with molecular weights of 2000 or less, and has a free amino acid content of less than 20% by mass.

Item 8. The method according to item 6 or 7, wherein in the first step, a polyphenol coexists in the solvent.

Item 9. The method according to any one of items 6 to 8, wherein air is used as the gas containing oxygen.

Advantageous Effects of Invention

According to the present invention, a gardenia blue pigment that exhibits a vivid blue tone that is bright and has reduced redness can be produced using a simple method. Moreover, the gardenia blue pigment of the present invention is a natural pigment, yet exhibits a blue tone similar to Food Blue No. 1, and thus, can color various products such as food products in a good color tone, with high safety. Furthermore, the gardenia blue pigment of the present invention can maintain the vivid blue tone that is bright and has reduced redness, even after it is subjected to a filtration treatment, a heat sterilization treatment, a drying treatment, and the like, which enables the production control to be simplified.

In one embodiment of the present invention, there is also provided a gardenia blue pigment having the property of stably maintaining the color tone even after heating under acidic conditions, in addition to having a vivid blue tone that is bright and has reduced redness, and thus, the gardenia blue pigment can also color acidic food products in a good color tone.

DESCRIPTION OF EMBODIMENTS

1. Gardenia Blue Pigment

A gardenia blue pigment of the present invention has a feature in that when prepared as a solution with a color value $E^{10\%}_{1\ cm}$ of 0.1 by diluting with water, the gardenia blue pigment has an L* value of 66 or more and an a* value of −24 or less in the Lab color space. Hereinafter, the gardenia blue pigment of the present invention will be described in detail.

[Color Tone Characteristics]

As used herein, "color value $E^{10\%}_{1\ cm}$" is the unit for expressing the color intensity of the pigment, and refers to the value obtained by measuring the absorbance at the maximum absorption wavelength in a reliable range of concentrations using an absorbance meter with a cell having an optical path length of 1 cm, and converting the absorbance to the value for a 10% by weight solution.

Since the maximum absorption wavelength of gardenia blue pigment is around 600 nm, the color value $E^{10\%}_{1\ cm}$ of the gardenia blue pigment can be determined by measuring the absorbance at a maximum absorption wavelength specified around 600 nm. If there is no maximum absorption wavelength, the absorbance at 600 nm can be measured.

The solution of the gardenia blue pigment with a color value $E^{10\%}_{1\ cm}$ of 0.1 is prepared by diluting the gardenia blue pigment with water (preferably ion-exchanged water). As used herein, "a color value $E^{10\%}_{1\ cm}$ of 0.1" means that when the value of color value $E^{10\%}_{1\ cm}$ is rounded off to three decimal places, it is 0.100.

The gardenia blue pigment of the present invention, when prepared as a solution with a color value $E^{10\%}_{1\ cm}$ of 0.1 by diluting with water, has an L* value of 66 or more in the Lab color space (CIE L*a*b* color space), and exhibits a bright blue tone. From the viewpoint of imparting a brighter blue tone, the L* value is preferably 66 to 75, more preferably 67 to 75, and even more preferably 68 to 73.

The gardenia blue pigment of the present invention, when prepared as a solution with a color value $E^{10\%}_{1\ cm}$ of 0.1 by diluting with water, has an a* value of −24 or less in the Lab color space, and exhibits a blue tone with little redness. From the viewpoint of imparting a blue tone with further reduced redness, the a* value is preferably −35 to −24, more preferably −35 to −25, and even more preferably −32 to −26.

The gardenia blue pigment of the present invention, when prepared as a solution with a color value $E^{10\%}_{1\ cm}$ of 0.1 by diluting with water, may have a b* value of −30 or more, for example, in the Lab color space, although not limited thereto. The b* value is preferably −27 or more, more preferably −25 or more, even more preferably −25 to −15, still more preferably −24 to −15, and particularly preferably −23 to −18.

The c* value (chroma) in the Lab color space is calculated according to $(a^{*}\ value^2 + b^{*}\ value^2)^{1/2}$. Thus, the c* value (chroma) in the Lab color space of the gardenia blue pigment of the present invention, when prepared as a solution with a color value $E^{10\%}_{1\ cm}$ of 0.1 by diluting with water, is defined in the range where the a* value and the b* value fall in the above-mentioned ranges. For example, the c* value (chroma) is 34 or more, preferably 35 to 40, more preferably 36 to 40, and even more preferably 37 to 40.

The h* value (hue) in the Lab color space of the gardenia blue pigment of the present invention, when prepared as a solution with a color value $E^{10\%}_{1\ cm}$ of 0.1 by diluting with water, is, for example, 230 or less, preferably 205 to 228, more preferably 205 to 225, and even more preferably 205 to 220, although not limited thereto.

The gardenia blue pigment of the present invention that satisfies such a color tone can be obtained using the method described below.

Conventional gardenia blue pigments have the drawback that when heated under acidic conditions, they become strongly reddish, and change in color tone. In contrast, when rice peptide is used as the peptide to be added in the first step of the below-described method, a gardenia blue pigment can be obtained which overcomes the above-described drawback of conventional gardenia blue pigments, and has the property of stably maintaining the color tone even after heating under acidic conditions (hereinafter, this property may be referred to as "acidic heating resistance"), while having the above-described color tone.

Specific examples of the gardenia blue pigment of the present invention having such acidic heating resistance include a gardenia blue pigment in which, when the gardenia blue pigment is subjected to operations as set forth in (1) to (3) below, a color difference $\Delta E^*_{ab}$ between solution A heat-treated at 90° C. for 15 minutes and solution B not heat-treated is 3.5 or less, and solution A heat-treated at 90° C. for 15 minutes has an L* value of 64 or more, an a* value of −14 or less, and a b* value of −31 or more:

<Operation Conditions>
(1) Preparation the gardenia blue pigment is diluted with 0.1 M citrate buffer at pH 2.5 to prepare solution A with a color value $E^{10\%}_{1\ cm}$ of 0.1; separately, the gardenia blue pigment is diluted with 0.1 M citrate buffer at pH 6.0 to prepare solution B with a color value $E^{10\%}_{1\ cm}$ of 0.1;

(2) Heat-Treatment of the Solutions solution A is heat-treated at 90° C. for 15 minutes; solution B is not heat-treated;

(3) Measurement of Color Tone for solution A heat treated at 90° C. for 15 minutes and solution B not heat-treated, the L* value, the a* value, and the b* value in the Lab color space are measured.

While the color difference $\Delta E^*_{ab}$ between solution A heat-treated at 90° C. for 15 minutes and solution B not heat-treated may be 3.5 or less, it is preferably 3.0 or less, more preferably 0 to 2.5, and even more preferably 0 to 2.0, from the viewpoint of imparting higher acidic heating resistance.

While the L value of solution A heat-treated at 90° C. for 15 minutes may be 64 or more, it is preferably 65 or more, more preferably 65 to 70, and even more preferably 66 to 70, from the viewpoint of imparting higher acidic heating resistance.

While the a* value of solution A heat-treated at 90° C. for 15 minutes may be −14 or less, it is preferably −15 or less, more preferably −26 to −16, and even more preferably −26 to −17, from the viewpoint of imparting higher acidic heating resistance.

While the b* value of solution A heat-treated at 90° C. for 15 minutes may be −31 or more, it is preferably −30 or more, more preferably −29 to −22, and even more preferably −28 to −22, from the viewpoint of imparting higher acidic heating resistance.

As used herein, the values in the Lab color space are the values measured using a spectrophotometer (CM-5; KONICA MINOLTA JAPAN, INC.). The measurement conditions are as follows: total transmission measurement, a D65 light source, a field-of-view of 10°, a measurement diameter of 20 mm, and an irradiation diameter of 26 mm.

The maximum absorption wavelength of conventional gardenia blue pigments is present around 600 nm, while the maximum absorption wavelength of the gardenia blue pigment of the present invention may be present in the range of, for example, 604 nm or more, preferably 605 or more, and more preferably 605 to 610.

[Use]

The gardenia blue pigment of the present invention is used as a blue colorant. While the products for which the gardenia blue pigment of the present invention is used are not limited as long as they require the use of a blue colorant, specific examples include food or beverage products, cosmetics, preparations for oral cavity, and pharmaceuticals. The gardenia blue pigment of the present invention, which is naturally derived and has high safety, is particularly suitable as a colorant for food or beverage products.

The food or beverage products to be colored with the gardenia blue pigment of the present invention are not limited in type, as long as they are required to be colored blue. Examples include confectioneries, such as jellies, gums, gummies, agar, cakes, cookies, and tablet candy; Japanese confectioneries, such as dumplings, rice cake sweets, bracken-starch dumplings (warabimochi), and bean pastes; processed fruit products, such as fruit sauces; jams, such as strawberry jam and blueberry jam; syrup; seasonings, such as Japanese sweetened sake (mirin), cooking liquor, dressings/dipping sauces, and sauces; frozen desserts, such as ice creams, iced milk, and ice desserts; dairy products, such as yogurt, ice creams, and whipped cream; seafood paste products, such as boiled fish pastes, fish cake tubes, fish meat sausages, and fish meat pastes; bottled and canned products, such as meat, fish meat, and fruits; beverages, such as lactic acid bacteria beverages, soft drinks, carbonated beverages, fruit juices, non-fruit beverages, fruit beverages, vegetable beverages, sport drinks, powdered beverages, jelly drinks, and alcoholic beverages; pickles; and noodles.

When the gardenia blue pigment of the present invention has acidic heating resistance, it is suitable for use in acidic food or beverage products, particularly acidic food or beverage products that are heat-sterilized in the manufacturing process. As used herein, the acidic food or beverage products refers to food or beverage products with a pH of 5.0 or less.

When the gardenia blue pigment of the present invention has acidic heating resistance, the pH of the acidic food or beverage products to be colored with the gardenia blue pigment is not limited as long as it is in the range of 5.0 or less. For example, the gardenia blue pigment of the present invention can impart a stably maintained color tone to acidic food or beverage products with a pH of 4.0 or less. Specific examples of acidic food or beverage products include acidic beverages, such as lactic acid bacteria beverages, soft drinks, carbonated beverages, fruit juices, non-fruit beverages, fruit beverages, vegetable beverages, sport drinks, jelly drinks, and alcoholic beverages; dairy products, such as yogurt, ice creams, and whipped cream; desserts, such as jellies; frozen desserts, such as sorbets, iced milk, and ice desserts; confectioneries, such as gummies and jelly beans; jams, such as strawberry jam and blueberry jam; sauces, such as fruit-flavored sauces; pickles; and seasonings, such as dressings.

The cosmetics to be colored with the gardenia blue pigment of the present invention are not limited in type, as long as they are required to be colored blue. Examples include basic skin care products, such as creams, emulsions, toners, essences, ointments, oils, packs, lotions, and gels; and makeup cosmetics, such as foundations, eyeshadows, lipsticks, and blushes.

The preparations for oral cavity to be colored with the gardenia blue pigment of the present invention are not limited in type, as long as they are required to be colored blue. Examples include dentifrices, such as paste, powder, and liquid dentifrices; tooth creams; mouth rinses, such as mouthwashes and gargles; pastes for oral cavity, mouth sprays, oral disintegrating films, gels, troches, tablets, and chewable tablets.

The pharmaceuticals to be colored with the gardenia blue pigment of the present invention are not limited in type, as long as they are required to be colored blue. Examples include powders, granules, tablets, capsules, pills, and liquids.

The amount of the gardenia blue pigment of the present invention to be added to the product to be colored may be set appropriately according to the type of the product and the degree of coloring to be applied to the product.

2. Method for Producing Gardenia Blue Pigment

A method for producing a gardenia blue pigment of the present invention has a feature in that it comprises the first and second steps as set forth below. The method for producing a gardenia blue pigment of the present invention will be hereinafter described in detail.

First step: reacting at least one peptide selected from the group consisting of soy peptide, sesame peptide, and rice peptide with genipin in a solvent without the supply of a gas containing oxygen.

Second step: treating the reaction solution obtained in the first step with the supply of a gas containing oxygen.

[First Step]

Peptide in the first step, at least one selected from the group consisting of soy peptide, sesame peptide, and rice peptide is used as a primary amino group-containing compound.

Soy peptide is a peptide with a low molecular weight obtained by hydrolysis of a soybean-derived protein. The hydrolysis of the soybean-derived protein may be carried out using any known method without limitation, for example, protease treatment, acid treatment, or alkali treatment. The soy peptide may also be a commercial product.

Sesame peptide is a peptide with a low molecular weight obtained by hydrolysis of a sesame-derived protein. The hydrolysis of the sesame-derived protein may be carried out using any known method without limitation, for example, protease treatment, acid treatment, or alkali treatment. The sesame peptide may also be a commercial product.

Rice peptide is a peptide with a low molecular weight obtained by hydrolysis of a rice-derived protein. The hydrolysis of the rice-derived protein may be carried out using any known method without limitation, for example, protease treatment, acid treatment, or alkali treatment. The rice peptide may also be a commercial product. As described above, when rice peptide is used as a primary amino group-containing compound, a gardenia blue pigment can be produced which not only exhibits a vivid blue tone that is bright and has reduced redness, but also has acidic heating resistance.

The average molecular weight of the soy peptide, sesame peptide, and rice peptide used in the present invention is, for example, about 5000 or less, preferably about 150 to 3000, and more preferably about 150 to 2000, although not limited thereto. The molecular weight distribution of the soy peptide, sesame peptide, and rice peptide is such that the ratio of peptides with molecular weights of 2000 or less is about 45% or more, preferably about 50 to 100%, and more preferably about 60 to 100. When this ratio of peptides with molecular weights of 2000 or less is contained, the gardenia blue pigment can be further improved in brightness and further reduced in redness. As used herein, the average molecular weight of the peptide is the weight average molecular weight calculated by gel filtration chromatography using HPLC, using peptides of known molecular weights as standards. The ratio of peptides with molecular weights of 2000 or less is the ratio of the peak area of peptides with molecular weights of 2000 or less to the total peak area.

A peptide may also contain free amino acids (amino acids that are not bound to the peptide, and present alone) produced upon hydrolysis of the protein. The inclusion of a large number of such free amino acids in the soy peptide, the sesame peptide, and the rice peptide may lead to reduced brightness and increased redness of the gardenia blue pigment. Thus, the soy peptide, sesame peptide, and rice peptide used in the present invention preferably contain less free amino acids; for example, the free amino acid content is less than 20% by mass, preferably 10% by mass or less, and more preferably 5% by mass or less.

Genipin

Genipin is an aglycone of geniposide (iridoid glycoside) contained in the fruit of *Gardenia jasminoides* Ellis of Rubiaceae. Genipin can be obtained by the action of a β-glucosidase on geniposide obtained by subjecting the fruit of *Gardenia jasminoides* Ellis of Rubiaceae to an extraction treatment.

The fruit of *Gardenia jasminoides* Ellis of Rubiaceae used for the extraction of geniposide may be an undried, dried, or frozen product. For higher extraction efficiency, the fruit of *Gardenia jasminoides* Ellis of Rubiaceae may be shredded or pulverized.

Examples of extraction solvents used for the extraction of geniposide include water, organic solvents, and mixed solvents thereof. Preferred organic solvents are hydrophilic organic solvents, for example, monohydric alcohols with 1 to 5 carbon atoms (e.g., ethanol, methanol, propanol, and isopropanol), polyhydric alcohols with 2 to 5 carbon atoms (e.g., glycerin, isopropylene glycol, propylene glycol, and 1,3-butylene glycol), esters (e.g., methyl acetate), and ketones (e.g., acetone). From the viewpoint of safety and active-ingredient extraction efficiency, preferred among these extraction solvents are water, lower monohydric alcohols, and mixed solvents thereof; more preferred are water, ethanol, and hydrous ethanol (mixed solvent of water and ethanol); and even more preferred is hydrous ethanol. When a mixed solvent of a lower monohydric alcohol and water is used as the solvent, the mixture ratio between the monohydric lower alcohol and water may be such that, for example, the concentration of the lower monohydric alcohol is about 1 to 99% by mass, preferably about 40 to 90% by mass, and more preferably about 50 to 80% by mass, although not limited thereto.

The extraction method may be any common solvent extraction method without limitation, for example, a method in which the crude drug is immersed in the extraction solvent by cold extraction, hot extraction, or the like, and optionally stirred; and a percolation method.

Geniposide can be recovered by optionally subjecting the extract obtained by the extraction treatment to filtration, centrifugation, or the like to remove solids. The recovered geniposide may be optionally subjected to a purification treatment, such as an adsorption treatment or gel filtration, to increase the purity.

The β-glucosidase used to produce genipin from geniposide may be any enzyme having β-glucosidase activity, for example, a β-glucosidase from *Aspergillus niger, Trichoderma reesei, Trichoderma viride*, or almonds. The enzyme having β-glucosidase activity may be a commercial product. Examples of commercial enzymes having β-glucosidase activity include Sumizyme C6000, Sumizyme AC, Sumizyme C, Sumizyme X, Sumizyme BGT, Sumizyme BGA (trade name; SHINNIHON CHEMICALS CORPORATION), Cellulosin AC40, Cellulosin T3, Cellulosin AL (trade name; HBI ENZYMES INC.), Onozuka 3S, Y-NC (trade name; YAKULT PHARMACEUTICAL INDUSTRY CO., LTD.), Cellulase A "Amano" 3, and Cellulase T "Amano" 4 (trade name; AMANO ENZYME INC.).

To produce genipin by the action of a β-glucosidase on geniposide, the β-glucosidase and geniposide may coexist under conditions that allow the β-glucosidase to act. The amount of the β-glucosidase to be used may be set appropriately according to conditions such as geniposide concentration, reaction temperature, and reaction time.

While the temperature condition for allowing the β-glucosidase to act may be set appropriately in the temperature range where the β-glucosidase acts, it is, for example, about 30 to 60° C., and preferably about 40 to 50° C.

While the pH condition for allowing the β-glucosidase to act may be set appropriately in the pH range where the β-glucosidase acts, it is, for example, about pH 3.5 to 6.0, and preferably about pH 4.3 to 4.8.

Examples of reaction solvents for allowing the β-glucosidase to act include water; and buffer solutions, such as a phosphate buffer solution, a citrate buffer solution, a Tris buffer solution, a tartrate buffer solution, and a borate buffer solution.

While the time for the β-glucosidase to act may be set appropriately according to the amounts of the β-glucosidase and the geniposide used, the temperature condition, and the like, it is, for example, about 3 to 30 hours, and preferably about 5 to 24 hours.

The reaction solution containing genipin produced by the action of the β-glucosidase on geniposide may be used as is as a genipin-containing solution in the first step, or may be optionally subjected to a purification treatment, a concentration treatment, a drying treatment, or the like to give a concentrate or a dried product, and used in the first step.

Polyphenol

In the first step, the reaction may be carried out in the presence of a polyphenol, together with the specific peptide and genipin. A polyphenol is a compound with a plurality of phenolic hydroxyl groups in the molecule. The polyphenol to be used may be of any origin, and may be any of polyphenols from plants, microbially produced polyphenols, chemically synthesized polyphenols, and other polyphenols, without limitation.

The polyphenol is not limited in type, and may be either a flavonoid polyphenol or a non-flavonoid (phenolic acid) polyphenol. Examples of flavonoid polyphenols include flavanones, flavones, flavonols, flavanols, flavanonols, isoflavones, anthocyanins, chalcones, and stilbenoids.

Specific examples of flavanones include hesperidin, glycosyl hesperetin, hesperetin, naringin, and liquiritigenin. Glucosyl hesperidin is a hesperidin derivative obtained by transferring a monosaccharide or an oligosaccharide, such as glucose, arabinose, galactose, rutinose, sophorose, or glucuronic acid, to a hydroxyl group of hesperidin. Specific examples of glucosyl hesperidin include α-monoglucosyl hesperidin, α-diglucosyl hesperidin, α-triglucosyl hesperidin, α-tetraglucosyl hesperidin, and α-pentaglucosyl hesperidin.

Specific examples of flavones include flavone, apigenin, luteolin, apigeninidin, luteolinidin, and baicalein.

Specific examples of flavonols include quercetin, kaempferol, and myricetin.

Specific examples of flavanols include catechins (e.g., epicatechin, epicatechin gallate, epigallocatechin, epigallocatechin gallate, and theaflavin), theaflavin, and leucoanthocyanidin.

Specific examples of flavanonols include alpinone and taxifolin.

Specific examples of isoflavones include genistein, daidzein, daidzin, glycitein, equol, biochanin A, coumestrol, puerarin, and formononetin.

Specific examples of anthocyanins include pelargonidin, cyanidin, petunidin, peonidin, petunidin, delphinidin, and malvidin.

Specific examples of chalcones include carthamin and phloretin.

Specific examples of stilbenoids include resveratrol.

Examples of non-flavonoid polyphenols include ellagic acid, coumarin, curcumin, chlorogenic acid, lignans, and sesamin.

These polyphenols may be used alone or in combination.

Preferred among these polyphenols are flavanones, more preferred are hesperidin, glycosyl hesperetin, and hesperetin, and even more preferred is glycosyl hesperetin.

The polyphenol may be in a purified form, or may be in the form of a mixture containing other components (e.g., an extract).

Reaction

In the first step, the specific peptide and genipin are reacted while they coexist in a solvent without the supply of a gas containing oxygen.

The concentration of the specific peptide and the concentration of genipin at the beginning of the reaction are, for example, as follows: the concentration of the specific peptide is about 1 to 50% by mass, preferably about 5 to 30% by mass, and more preferably about 10 to 20% by mass, while the concentration of genipin is about 0.1 to 50% by mass, preferably about 1 to 20% by mass, and more preferably about 2.5 to 10% by mass.

The proportion of the specific peptide to genipin at the beginning of the reaction is, for example, about 20 to 1000 parts by mass, preferably about 100 to 600 parts by mass, more preferably about 200 to 300 parts by mass, of the specific peptide, per 100 parts by mass of genipin.

When a polyphenol coexists, the polyphenol concentration at the beginning of the reaction is, for example, about 0.01 to 10% by mass, preferably about 0.025 to 5% by mass, and more preferably about 0.5 to 1% by mass. When the polyphenol coexists, the proportion of the polyphenol to genipin at the beginning of the reaction is, for example, about 0.2 to 220 parts by mass, preferably about 0.5 to 110 parts by mass, more preferably about 1 to 22 parts by mass, of the polyphenol, per 100 parts by mass of genipin.

The pH at which the specific peptide is reacted with genipin is, for example, about 5 to 10, preferably about 6 to 9, and more preferably about 7 to 8. During the reaction, the pH may be adjusted to remain constant in these pH ranges.

Examples of the solvent for reacting the specific peptide with genipin include water; and buffer solutions, such as a phosphate buffer solution, a citrate buffer solution, a Tris buffer solution, a tartarate buffer solution, and a borate buffer solution.

In the first step, the reaction of the specific peptide and genipin while they coexist in a solvent may be carried out using, for example, a method in which genipin is added to a solution in which the specific peptide is dissolved; or a method in which the specific peptide is added to a solution in which genipin is dissolved. When the reaction solution containing genipin produced by the action of the β-glucosidase (genipin-containing solution) is used, the specific peptide may be added to the reaction solution.

In the first step, the specific peptide and genipin are reacted while they coexist in a solvent, without supplying a gas containing oxygen. The reaction of the specific peptide and genipin without supplying a gas containing oxygen may be carried out using, for example, a method in which, in an air atmosphere, they are stirred sufficiently gently to prevent the incorporation of air, or they are left standing without stirring (hereinafter, "the first method"); a method in which they are stirred or left standing in the atmosphere of an inert gas, such as nitrogen gas or argon gas; or a method in which an inert gas, such as nitrogen gas or argon gas, is supplied into the solution. Preferred among these methods is the first method, which is simple because it does not require the preparation of an inert gas or special equipment.

The temperature during the reaction in the first step is, for example, about 5 to 50° C. preferably about 10 to 45° C., and more preferably about 20 to 40° C.

The reaction time in the first step is, for example, about 1 hour or more, preferably about 3 to 24 hours, and more preferably about 5 to 20 hours.

[Second Step]

In the second step, the reaction solution obtained in the first step is treated with the supply of a gas containing oxygen. The reaction solution obtained in the first step may be used as is in the second step; alternatively, it may be optionally adjusted to a pH of about 5 to 10, preferably about 6 to 9, more preferably about 7 to 8, and then subjected to the second step. During the reaction, the pH may be adjusted to remain constant in these pH ranges.

The gas containing oxygen used in the second step may be oxygen gas itself, or may be, for example, air or a like gas that contains a gas component other than oxygen. From the viewpoint of a reduction in production costs and the like, air is preferred as the gas containing oxygen.

The gas containing oxygen is supplied to the reaction solution obtained in the first step, using, for example, a method in which the gas containing oxygen is directly introduced into the reaction solution, and optionally stirred; or a method in which the reaction solution is stirred in the atmosphere of the gas containing oxygen so that the gas containing oxygen enters the reaction solution.

The supply amount of the gas containing oxygen may be similar to the aerobic conditions (conditions for color development) as employed in the manufacturing of conventional gardenia blue pigments, and may be set appropriately according to the size of the equipment for carrying out the second step, whether stirring is carried out or not during the supply of the gas containing oxygen, the stirring speed, and the like. For example, the supply amount of the gas containing oxygen is 0.01 to 5.0 vvm, preferably 0.05 to 2.5 vvm, and more preferably 0.1 to 1.0 vvm. As used herein, the unit "vvm" for the supply amount of the gas containing oxygen refers to the amount of the gas supplied in 1 minute per liter of the reaction solution obtained in the first step. As used herein, the exemplary amounts of the gas containing oxygen are expressed as the speed of supply of air itself. Specifically, for example, when pure oxygen gas is used as the gas containing oxygen, because air contains about 20% by volume of oxygen, the oxygen gas may be supplied in an amount of 20% by volume of the above-described supply amount.

The temperature at which the gas containing oxygen is supplied is, for example, about 5 to 50° C., preferably about 10 to 45° C., and more preferably about 20 to 40° C. The temperature during the second step may be constant, or may vary in these ranges during the reaction.

In the second step, the supply of the gas containing oxygen may be carried out until the color value of the solution becomes constant; alternatively, it may be stopped when the desired color tone is exhibited. Specifically, the time for supplying the gas containing oxygen is 1 hour or more, preferably about 3 to 120 hours, more preferably about 6 to 50 hours, and even more preferably about 12 to 40 hours.

By thus carrying out the second step, the above-described gardenia blue pigment is produced which exhibits a vivid blue tone that is bright and has reduced redness. The reaction solution after the second step may be used as is, as the gardenia blue pigment solution; alternatively, it may be optionally subjected to a purification treatment, a concentration treatment, a drying treatment, or the like to give a concentrate or a dried product of the gardenia blue pigment.

EXAMPLES

The present invention will be hereinafter described in detail based on examples and the like, although the present invention is not limited thereto.

Text Example 1

1. Production of Gardenia Blue Pigment (Using Jar Fermenter) (Examples 1-1 to 1-3 and Comparative Examples 1-1 to 1-15)
(1) Preparation of Genipin First, a geniposide solution (color value $E^{10\%}_{1\ cm}$: 1335.48; measurement wavelength: 238 nm; geniposide content: about 45% by mass) extracted and purified from the fruit of *Gardenia jasminoides* Ellis of Rubiaceae was prepared. 11.0 g of a β-glucosidase activity-containing cellulase (SUMIZYME C, 1500 U/g; SHINNIHON CHEMICALS CORPORATION) was dissolved in 110 g of purified water, and 110 g of the geniposide solution (color value $E^{10\%}_{1\ cm}$ at the beginning of the reaction: 245; measurement wavelength: 238 nm; geniposide concentration at the beginning of the reaction: about 0.2 mol/L) was added thereto. Then, after the pH of the solution was adjusted to 4.5, the enzymatic reaction was carried out at 50° C. for 18 hours to obtain a genipin-containing solution (solution after the reaction).
(2) Reaction under Conditions without Supply of Oxygen Gas 5.5 g of sodium dihydrogen phosphate dihydrate, 4.27 g of trisodium phosphate (anhydrous), and 76.1 g of each peptide or amino acid shown in Table 1 were added to and dissolved in 283 g of water. The obtained solution was mixed into the (entire amount of) genipin-containing solution obtained above, and the pH of the mixture was adjusted to 7.5. The obtained solution was transferred into a 1-L jar fermenter (BMJ-01NC; ABLE CORPORATION), and reacted for 15 hours without aeration, under stirring conditions sufficiently gentle to prevent the incorporation of air, at 35° C.
(3) Reaction Under Conditions with Supply of Oxygen Gas After the reaction solution after the reaction under conditions without the supply of oxygen gas was adjusted to pH 7.0, the reaction was carried out under stirring conditions at 420 rpm and 35° C., while supplying air to the reaction solution at a supply amount of 0.25 vvm, until the increase in color value leveled off. The reaction time was 24 to 48 hours, although the reaction time varied with the peptide or amino acid used. In this manner, a gardenia blue pigment-containing solution (solution after the reaction) was obtained.

2. Measurement of Color Tone of Gardenia Blue Pigment

The obtained gardenia blue pigment-containing solution was filtered, and the pigment solution from which insoluble matter was removed was diluted with ion-exchanged water to prepare a solution with a color value of $E^{10\%}_{1\ cm}$ of 0.1. The color tone of this solution was measured using a spectrophotometer (CM-5; KONICA MINOLTA JAPAN, INC.). The measurement conditions were set as follows: total transmission measurement, a D65 light source, a field-of-view of 10°, a measurement diameter of 20 mm, and an irradiation diameter of 26 mm. For reference, Food Blue No. 1 was diluted with ion-exchanged water to prepare a solution with a color value of $E^{10\%}_{1\ cm}$ of 0.1, and the color tone of this solution was also measured in the same manner.

The results are shown in Table 1. The results confirmed that the gardenia blue pigments obtained by reacting soy peptide, sesame peptide, or rice peptide with genipin without the supply of air, and then reacting the reaction solution with the supply of air, when prepared as a solution with a color value $E^{10\%}_{1\ cm}$ of 0.1, have an L* value of 66 or more and an a* value of −24 or less, and exhibit a vivid blue tone that is bright and has reduced redness, and produce a color tone more similar to Food Blue No. 1 than conventional gardenia blue pigments (Examples 1-1 to 1-3). In contrast, the gardenia blue pigments produced under the same conditions, using a peptide or an amino acid other than soy peptide, sesame peptide, and rice peptide, have a reddish blue color (high a* value), and failed to exhibit a color tone similar to Food Blue No. 1 (Comparative Examples 1-1 to 1-15).

TABLE 1

| | Peptide or amino acid added | Maximum absorption wavelength (nm) | L* value | a* value | b* value | c* value | h* value | ΔE*$_{ab}$ value[#3] |
|---|---|---|---|---|---|---|---|---|
| Example 1-1 | Soy peptide (Hinute-AM; FUJI OIL CO., LTD )[#1] | 605.5 | 67.74 | −26.45 | −22.35 | 34.63 | 220.20 | 24.41 |
| Example 1-2 | Sesame peptide (Sesame peptide KM-20; MARUZEN PHARMACEUTICALS CO., LTD.)[#2] | 609.5 | 65.75 | −30.81 | −20.98 | 37.27 | 214.25 | 25.25 |
| Example 1-3 | Rice peptide (Rice peptide powder; WUHAN TALLYHO BIOLOGICAL PRODUCT CO., LTD.) | 604.5 | 70.19 | −27.66 | −24.53 | 36.97 | 221.57 | 22.20 |
| Comparative Example 1-1 | Fish collagen peptide (Fish collagen tripeptide; WUHAN TALLYHO BIOLOGICAL PRODUCT CO., LTD.) | 600.0 | 67.11 | −22.75 | −29.08 | 36.92 | 231.96 | 28.05 |
| Comparative Example 1-2 | Walnut peptide (Walnut peptide powder; WUHAN TALLYHO BIOLOGICAL PRODUCT CO., LTD.) | 602.0 | 66.67 | −22.4 | −29.15 | 36.76 | 232.46 | 28.58 |
| Comparative Example 1-3 | Pea peptide (Pea peptide powder; WUHAN TALLYHO BIOLOGICAL PRODUCT CO., LTD.) | 602.0 | 67.28 | −22.23 | −30.03 | 37.36 | 233.49 | 28.48 |
| Comparative Example 1-4 | Sea cucumber peptide (Sea cucumber oligopeptide; DALIAN BLUESCITECH TECHNOLOGY RESEARCH AND DEVELOPMENT CO., LTD.) | 598.5 | 66.07 | −21.11 | −28.06 | 35.11 | 233.05 | 29.26 |
| Comparative Example 1-5 | Bitter melon peptide (Bitter melon peptide powder; WUHAN TALLYHO BIOLOGICAL PRODUCT CO., LTD.) | 600.0 | 65.5 | −19.66 | −31.04 | 36.74 | 237.65 | 31.43 |
| Comparative Example 1-6 | Gelatin peptide (SCP-3100; NITTA GELATIN INC.) | 598.0 | 62.37 | −17.04 | −26.64 | 31.62 | 237.40 | 33.89 |
| Comparative Example 1-7 | Casein peptide (Kyokuto peptide; KYOKUTO PHARMACEUTICAL INDUSTRIAL CO., LTD) | 597.5 | 62.49 | −15.67 | −31 | 34.74 | 243.18 | 35.73 |
| Comparative Example 1-8 | Corn peptide (AMIFLEX AL-1; MC FOOD SPECIALTIES INC.) | 592.5 | 62.69 | −13.57 | −30.71 | 33.57 | 246.16 | 36.60 |
| Comparative Example 1-9 | Wheat peptide (Pro Ekisu HVP-G; BANSHU CHOMIRYO CO., LTD.) | 593.0 | 62.45 | −13.49 | −30.71 | 33.54 | 246.29 | 36.83 |
| Comparative Example 1-10 | Potato peptide (Amino acid gold; COSMO FOOD CO., LTD.) | 592.0 | 62.52 | −12.08 | −30.29 | 32.61 | 248.26 | 37.44 |
| Comparative Example 1-11 | Silk powder peptide (Tango silk powder 100%; TANGO YOU SILK, LTD.) | 589.0 | 61.46 | −6.03 | −31.31 | 31.89 | 259.10 | 42.28 |
| Comparative Example 1-12 | Histidine | 595.5 | 67.09 | −17.74 | −29.61 | 34.52 | 239.07 | 30.58 |
| Comparative Example 1-13 | Glutamic acid | 593.0 | 66.22 | −13.51 | −31.37 | 34.16 | 246.70 | 34.24 |

TABLE 1-continued

| | Peptide or amino acid added | Maximum absorption wavelength (nm) | Measurement results | | | | | |
|---|---|---|---|---|---|---|---|---|
| | | | L* value | a* value | b* value | c* value | h* value | ΔE*$_{ab}$ value[#3] |
| Comparative Example 1-14 | Arginine | 598.5 | 67.82 | −19.91 | −28.75 | 34.97 | 235.30 | 28.60 |
| Comparative Example 1-15 | Aspartic acid | 593.0 | 67.25 | −16.64 | −30.94 | 35.13 | 241.73 | 31.54 |
| Reference Example (Food Blue No. 1; KYORITSU FOODS CO., INC.) | | 630.0 | 90.72 | −33.86 | −18.79 | 38.72 | 209.03 | Reference |

[#1] In "Soy peptide (Hinute-AM; FUJI OIL CO., LTD.)", the free amino acid content is 2% by mass, and the peak area of peptides with molecular weights of 2000 or less to the total peak area is 78.1%, as analyzed by gel filtration chromatography using HPLC.
[#2] In "Sesame peptide (Sesame peptide KM-20; MARUZEN PHARMACEUTICALS CO., LTD.)", the peak area of peptides with molecular weights of 2000 or less to the total peak area is 90% or more, as analyzed by gel filtration chromatography using HPLC.
[#3] The ΔE*$_{ab}$ value represents the value of the color difference relative to Food Blue No. 1 (Reference Example) as the reference.

Additionally, each of the gardenia blue pigment-containing solutions obtained in Examples 1-1 to 1-3 was filtered, and the pigment solution from which insoluble matter was removed was diluted with ion-exchanged water to prepare a solution with a color value of $E^{10\%}_{1\ cm}$ of 0.05. The color tone of this solution was measured using a UV-visible spectrophotometer (JASCO; V750) equipped with an integrating sphere. The results are shown in Table 2. The results also confirmed that the gardenia blue pigments obtained in Examples 1-1 to 1-3 exhibit a vivid blue tone that is bright and has reduced redness.

TABLE 2

| | Peptide added | Measurement results | | |
|---|---|---|---|---|
| | | L* value | a* value | b* value |
| Example 1-1 | Soy peptide | 76.07 | −17.36 | −16.42 |
| Example 1-2 | Sesame peptide | 77.09 | −18.82 | −15.03 |
| Example 1-3 | Rice peptide | 74.93 | −15.84 | −17.41 |

Text Example 2

1. Production of Gardenia Blue Pigment (Using Jar Fermenter) (Examples 2-1 to 2-5)

Gardenia blue pigments were produced as in Test Example 1, except that the soy peptides shown in Table 3 were used in the reaction under conditions without the supply of oxygen gas.

2. Measurement of Color Tone of Gardenia Blue Pigment

The color tone of each of the obtained gardenia blue pigments was measured under the same conditions as in Test Example 1. The results are shown in Table 3. The results confirmed that when a predetermined peptide is reacted with genipin without the supply of air, and then the reaction solution is reacted with the supply of air, the color tone of the obtained gardenia blue pigment becomes better with less redness, as the free amino acid content in the peptide used decreases.

TABLE 3

| | Peptide used | | | Measurement results | | | | |
|---|---|---|---|---|---|---|---|---|
| | Trade name | Free amino acid content (% by mass) | Ratio (%) of peptides with molecular weights of 2000 or less[#] | L* value | a* value | b* value | c* value | h* value |
| Example 2-1 | Soy peptide (Soy peptide powder; WUHAN TALLYHO BIOLOGICAL PRODUCT CO., LTD.) | Not measured | 80.0 | 66.8 | −28.2 | −23.53 | 36.73 | 219.84 |
| Example 2-2 | Soy peptide (Hinute-AM; FUJI OIL CO., LTD.) | 2 | 78.1 | 67.74 | −26.45 | −22.35 | 34.63 | 220.20 |
| Example 2-3 | Soy peptide (Hinute-DA; FUJI OIL CO., LTD.) | 5 | 76.8 | 69.18 | −27.81 | −24.28 | 36.92 | 221.12 |
| Example 2-4 | Soy peptide (Hinute-DC6; FUJI OIL CO., LTD.) | 2 | 61.1 | 66.61 | −26.3 | −23.86 | 35.51 | 222.22 |
| Example 2-5 | Soy peptide (Hinute-D1; FUJI OIL CO., LTD.) | 1 | 45.8 | 65.98 | −26.6 | −23.92 | 35.77 | 221.96 |

[#] "Ratio (%) of peptides with molecular weights of 2000 or less" is the value determined as the peak area of peptides with molecular weights of 2000 or less to the total peak area, as analyzed by gel filtration chromatography using HPLC.

Text Example 3

1. Production of Gardenia Blue Pigment (Using Jar Fermenter) (Examples 3-1 to 3-3 and Comparative Example 3-1)

Gardenia blue pigments were produced as in Test Example 1, except that soy peptide (Hinute-AM; FUJI OIL CO., LTD.) was used as the peptide to be added, and the reaction time under conditions without the supply of oxygen gas was changed to 0 hour (Comparative Example 3), 4 hours (Example 3-1), 5 hours (Example 3-2), or 22 hours (Example 3-3).

2. Production of Gardenia Blue Pigment (Using Jar Fermenter) (Comparative Example 3-2)

(1) Preparation of Genipin

The genipin-containing solution was prepared under the conditions set forth in Test Example 1.

(2) Reaction under Conditions with Supply of Oxygen Gas 5.5 g of sodium dihydrogen phosphate dihydrate, 4.27 g of trisodium phosphate (anhydrous), and 76.1 g of the peptide or amino acid as shown in Table 4 were added to and dissolved in 283 g of water. The obtained solution was mixed into the (entire amount of) genipin-containing solution obtained above, and the pH of the mixture was adjusted to 7.5. The obtained solution was transferred into a 1-L jar fermenter, and the reaction was carried out under stirring conditions at 420 rpm and 35° C., while supplying air to the solution at a supply amount of 0.25 vvm, until the increase in color value leveled off. The reaction time was 33 hours.

(3) Reaction Under Conditions without Supply of Oxygen Gas

After the reaction solution after the reaction under conditions with the supply of oxygen gas was adjusted to pH 7.0, it was reacted for 18 hours without aeration, under stirring conditions sufficiently gentle to prevent the incorporation of air, at 35° C. In this manner, a gardenia blue pigment-containing solution (solution after the reaction) was obtained.

3. Measurement of Color Tone of Gardenia Blue Pigment

The color tone of each of the obtained gardenia blue pigments was measured under the same conditions as in Test Example 1. The results are shown in Table 4. As shown in Table 4, Food Blue No. 1 was diluted with ion-exchanged water to prepare a solution with a color value of $E^{10\%}_{1\,cm}$ of 0.1, and the color tone of this solution was also measured in the same manner. The results also confirmed that when a predetermined peptide is reacted with genipin without the supply of air, and then the reaction solution is reacted with the supply of air, a gardenia blue pigment is obtained which exhibits a vivid blue tone that is bright and has reduced redness.

In contrast, when a predetermined peptide was reacted with genipin with the supply of air, and then the reaction solution was reacted without the supply of air, a gardenia blue pigment was not obtained which exhibits a vivid blue tone that is bright and has reduced redness.

TABLE 4

| | Reaction time (hrs) under conditions without supply of oxygen gas | Measurement results | | | | | |
|---|---|---|---|---|---|---|---|
| | | L* value | a* value | b* value | c* value | h* value | ΔE*$_{ab}$ value# |
| Comparative Example 3-1 | 0 | 65.87 | −19.56 | −30.99 | 36.65 | 237.74 | 31.16 |
| Example 3-1 | 4 | 67.60 | −25.71 | −28.45 | 38.35 | 227.90 | 26.35 |
| Example 3-2 | 5 | 67.89 | −26.44 | −26.80 | 37.65 | 225.39 | 25.31 |
| Example 3-3 | 22 | 67.97 | −25.93 | −28.14 | 38.27 | 227.34 | 25.84 |
| Comparative Example 3-2 (reaction without supply of oxygen was carried out after reaction with supply of oxygen) | | 66.33 | −22.09 | −28.59 | 36.13 | 232.31 | 28.80 |
| Reference Example (Food Blue No. 1; KYORITSU FOODS CO., INC.) | | 90.72 | −33.86 | −18.79 | 38.72 | 209.03 | — |

The ΔE*$_{ab}$ value represents the value of the color difference relative to Food Blue No. 1 (Reference Example) as the reference.

Text Example 4

1. Production of Gardenia Blue Pigment (Using Jar Fermenter) (Example 4-1)

A gardenia blue pigment was produced as in Test Example 1, except that soy peptide (Hinute-AM; FUJI OIL CO., LTD.) was used as the peptide to be added, and 1.2 g of glucosyl hesperidin (α-triglucosyl hesperidin content: 85% by mass, αG hesperidin PA-T; EZAKI GLICO CO., LTD.) was added to the solution to be subjected to the reaction under conditions without the supply of oxygen gas.

2. Production of Gardenia Blue Pigment (Using Flask) (Example 4-2)

(1) Preparation of Genipin

First, a geniposide solution (color value $E^{10\%}_{1\,cm}$: 1240; measurement wavelength: 238 nm; geniposide content: about 45% by mass) extracted and purified from the fruit of *Gardenia jasminoides* Ellis of Rubiaceae was prepared. 3.56 g of a β-glucosidase activity-containing cellulase (SUMIZYME C, 1500 U/g; SHINNIHON CHEMICALS CORPORATION) was dissolved in 39.11 g of purified water, and 35.5 g of the geniposide solution (color value $E^{10\%}_{1\,cm}$ at the beginning of the reaction: 245; measurement wavelength: 238 nm; geniposide concentration: about 0.2 mol/L) was added thereto. Then, after the pH of the solution was adjusted to 4.5, the enzymatic reaction was carried out at 50° C. for 18 hours to obtain a genipin-containing solution (solution after the reaction).

(2) Reaction under Conditions without Supply of Oxygen Gas 1.65 g of sodium dihydrogen phosphate dihydrate, 1.28 g of trisodium phosphate (anhydrous), 22.83 g of soy peptide (Hinute-AM; FUJI OIL CO., LTD.), and 0.18 g of glucosyl hesperidin (α-triglucosyl hesperidin content: 85% by mass, αG hesperidin PA-T; EZAKI GLICO CO., LTD.) were added to and dissolved in 75 g of water. The obtained solution was mixed into the (entire amount of) genipin-containing solution obtained above, and the pH of the mixture was adjusted to 7.5. The obtained solution was transferred into a 300-mL beaker, which was sealed, and reacted for 18 hours without aeration, under a stirring (magnetic stirrer) condition of 100 rpm at 35° C.

(3) Reaction under Conditions with Supply of Oxygen Gas

After the reaction solution after the reaction under conditions without the supply of oxygen gas was adjusted to pH 7.0, it was transferred into a 500-mL flask, and, with the mouth of the flask open to the air atmosphere, the reaction was carried out for 30 hours under a stirring condition of 150 rpm at 35° C., until the increase in color value leveled off. In this manner, a gardenia blue pigment-containing solution (solution after the reaction) was obtained.

3. Measurement of Color Tone of Gardenia Blue Pigment

Using the obtained gardenia blue pigment-containing solution, the color tone was measured as in Test Example 1. The results are shown in Table 5. Table 5 also shows the results obtained by measuring the color tone of a solution with a color value $E^{10\%}_{1\ cm}$ of 0.1 prepared by diluting Food Blue No. 1 with ion-exchanged water. The results confirmed that similarly when glucosyl hesperidin is added in the reaction of soy peptide and genipin under conditions without the supply of oxygen gas, if the reaction solution after the reaction without the supply of air is reacted with the supply of air, a gardenia blue pigment is obtained which exhibits a vivid blue tone that is bright and has reduced redness.

The maximum absorption wavelength of the gardenia blue pigment of Example 4-1 was 605.5 nm, and the maximum absorption wavelength of the gardenia blue pigment of Example 4-2 was 608.0 nm.

TABLE 5

| | Production conditions | | Measurement results | | | | | |
|---|---|---|---|---|---|---|---|---|
| | Equipment used for reaction | Addition of glucosyl hesperidin | L* value | a* value | b* value | c* value | h* value | ΔE*$_{ab}$ value[#] |
| Example 4-1 | Jar fermenter | Added | 70.75 | −28.74 | −25.61 | 38.49 | 221.70 | 21.71 |
| Example 4-2 | Flask | Added | 70.94 | −28.54 | −23.97 | 37.27 | 220.03 | 21.13 |
| Reference Example (Food Blue No. 1; KYORITSU FOODS CO., INC.) | | | 90.72 | −33.86 | −18.79 | 38.72 | 209.03 | — |

[#]The ΔE*$_{ab}$ value represents the value of the color difference relative to Food Blue No. 1 (Reference Example) as the reference.

Test Example 5

1. Production of Gardenia Blue Pigment (Using Flask) (Reference Example 1)

A gardenia blue pigment was produced in accordance with the method of Example 2 described in Patent Literature 3 (WO 2017/156744). Specifically, 0.6 g of genipin (purity 98%; GLICO NUTRITION CO., LTD.), 9 mL of 99.5% ethanol, and 2.05 g of sodium glutamate monohydrate were dissolved in water. The obtained solution was placed in a flask, which was placed in a water bath at 75° C., and reacted at 150 strokes/minute for 6 hours. The ethanol in the reaction solution after the reaction was removed with an evaporator, and then the reaction solution was lyophilized to obtain a gardenia blue pigment as a powder.

2. Measurement of Color Tone of Gardenia Blue Pigment

The obtained gardenia blue pigment was diluted with ion-exchanged water to prepare a solution with a color value $E^{10\%}_{1\ cm}$ of 0.0337, and the color tone of this solution was measured using a spectrophotometer (CM-5; KONICA MINOLTA JAPAN, INC.). The measurement conditions were set as follows: total transmission measurement, a D65 light source, a field-of-view of 10°, a measurement diameter of 20 mm, and an irradiation diameter of 26 mm. For reference, the gardenia blue pigment-containing solution obtained in Example 1-1 was diluted with ion-exchanged water to prepare a solution with a color value $E^{10\%}_{1\ cm}$ of 0.0337, and the color tone of this solution was also measured in the same manner.

The results are shown in Table 6. The results confirmed that the gardenia blue pigment obtained using the method of Patent Literature 3 has a high a* value, and exhibits a reddish tone.

TABLE 6

| | | Measurement results | | | | |
|---|---|---|---|---|---|---|
| | | L* value | a* value | b* value | c* value | h* value |
| Reference Example 1 | Solution with a color value $E^{10\%}_{1\ cm}$ of 0.0337 | 86.43 | −8.26 | −13.52 | 15.85 | 238.57 |
| Example 1-1 | Solution with a color value $E^{10\%}_{1\ cm}$ of 0.0337 | 85.37 | −14.51 | −13.15 | 19.58 | 222.19 |

Test Example 6

1. Production of Gardenia Blue Pigment (Using Flask) (Examples 5-1 and 5-2)
(1) Preparation of Genipin First, a geniposide solution (color value $E^{10\%}_{1\ cm}$: 1335.48; measurement wavelength: 238 nm; geniposide content: about 45% by mass) extracted and purified from the fruit of *Gardenia jasminoides* Ellis of Rubiaceae was prepared. 4.17 g of a β-glucosidase activity-containing cellulase (SUMIZYME C, 1500 U/g; SHINNIHON CHEMICALS CORPORATION) was dissolved in 41.67 g of purified water, and 41.67 g of the geniposide solution (color value $E^{10\%}_{1\ cm}$ at the beginning of the reaction: 245; measurement wavelength: 238 nm; geniposide concentration: about 0.2 mol/L) was added thereto. Then, after the pH of the solution was adjusted to 4.5, the enzymatic reaction was carried out at 50° C. for 18 hours to obtain a genipin-containing solution (solution after the reaction).

(2) Reaction Under Conditions without Supply of Oxygen Gas 1.65 g of sodium dihydrogen phosphate dihydrate, 1.28 g of trisodium phosphate (anhydrous), and 22.83 g of rice peptide (rice peptide powder; WUHAN TALLYHO BIOLOGICAL PRODUCT CO., LTD.) were added to and dissolved in 75 g of water. The obtained solution was mixed into the (entire amount of) genipin-containing solution obtained above, and the pH of the mixture was adjusted to 7.5. The obtained solution was transferred into a 300-mL beaker, which was sealed, and reacted for 18 hours without aeration, under a stirring (magnetic stirrer) condition of 100 rpm at 35° C.

(3) Reaction Under Conditions with Supply of Oxygen Gas

After the reaction solution after the reaction under conditions without the supply of oxygen gas was adjusted to pH 7.0, it was transferred into a 500-mL flask, and, with the mouth of the flask open to the air atmosphere, the reaction was carried out for 48 hours under a stirring condition of 150 rpm at 35° C., until the increase in color value leveled off. In this manner, a gardenia blue pigment-containing solution (solution after the reaction) was obtained.

2. Measurement of Acidic Heating Resistance of Gardenia Blue Pigment

The obtained gardenia blue pigment-containing solution was diluted with 0.1 M citrate buffer at pH 2.5 to prepare solution A (color value $E^{10\%}_{1\ cm}$: 0.1). Separately, the obtained gardenia blue pigment-containing solution was diluted with 0.1 M citrate buffer at pH 6.0 to prepare solution B (color value $E^{10\%}_{1\ cm}$: 0.1). After solutions A and B were left standing at 5° C. for about 18 hours, solution A was heat treated at 90° C. for 15 minutes. Solution B was not heat treated. Solutions A and B were centrifuged at 3,000 rpm for 10 minutes in a centrifuge, and the absorbance of the supernatant at the maximum absorption wavelength around 600 nm was measured. The ratio of the absorbance of solution A to the absorbance of solution B taken as 100% was determined as the residual ratio after the heat treatment at 90° C. for 15 minutes under a pH condition of 2.5.

Moreover, the color tones of solution A after the heat treatment and non-heat treated solution B (after being left standing at 5° C. for about 18 hours) were measured using a spectrophotometer (CM-5; KONICA MINOLTA JAPAN, INC.). The measurement conditions were set as follows: total transmission measurement, a D65 light source, a field-of-view of 10°, a measurement diameter of 20 mm, and an irradiation diameter of 26 mm.

The results are shown in Table 7. The results showed that the gardenia blue pigment obtained by reacting rice peptide with genipin under conditions without the supply of oxygen gas, and then reacting the reaction solution with the supply of oxygen gas, even after it is heated under a pH condition of 2.5 (color value $E^{10\%}_{1\ cm}$: 0.1), has an L* value of 64 or more, an a* value of −14 or less, and a b* value of −31 or more, and moreover, has a $\Delta E^*_{ab}$ of 3.5 or less in comparison with the non-heated solution under a pH condition of 6.0 (color value $E^{10\%}_{1\ cm}$: 0.1), and thus, has excellent acidic heating resistance.

TABLE 7

| | pH at the beginning of supply of oxygen gas | | Residual ratio (%) | L* value | a* value | b* value | c* value | $\Delta E^*_{ab}$ value[#] |
|---|---|---|---|---|---|---|---|---|
| Example 5-1 | 7.0 | Solution A after heat treatment (pH 2.5) | 97.63 | 66.75 | −21.98 | −24.01 | 32.55 | 2.89 |
| | | Non-heat treated solution B (pH 6.0) | — | 68.27 | −24.43 | −24.26 | 34.43 | 0.00 |

[#]The $\Delta E^*_{ab}$ value represents the value of the color difference relative to non-heat heated solution B as the reference.

Test Example 7

1. Production of Gardenia Blue Pigment (Using Flask) (Comparative Examples 7-1 to 7-5)

Gardenia blue pigments were produced under the same conditions as in Example 5-1, except that the peptides or amino acid as shown in Table 8 were used instead of the rice peptide.

2. Measurement of Acidic Heating Resistance of Gardenia Blue Pigment

Acidic heating resistance was measured under the same conditions as in Test Example 6. The results are shown in Table 8. The results confirmed that when a peptide other than rice peptide is reacted with genipin without the supply of air, and then the reaction solution is reacted with the supply of air, the obtained gardenia blue pigment fails to have acidic heating resistance.

TABLE 8

| | Peptide added | | L* value | a* value | b* value | c* value | $\Delta E^*_{ab}$ value[#] |
|---|---|---|---|---|---|---|---|
| | | | Measurement results | | | | |
| Comparative Example 7-1 | Silk powder peptide (Tango silk powder 100%; TANGO YOU SILK, LTD.) | Solution A after heat treatment (pH 2.5) | 64.38 | −1.27 | −25.04 | 25.07 | 5.72 |
| | | Non-heat treated solution B (pH 6.0) | 63.26 | −3.65 | −30.11 | 30.33 | — |
| Comparative Example 7-2 | Pea peptide (Pea peptide powder; WUHAN TALLYHO BIOLOGICAL PRODUCT CO., LTD.) | Solution A after heat treatment (pH 2.5) | 65.45 | −17.29 | −29.50 | 34.19 | 6.17 |
| | | Non-heat treated solution B (pH 6.0) | 68.96 | −17.31 | −24.42 | 29.93 | — |
| Comparative Example 7-3 | Sea cucumber peptide (Sea cucumber oligopeptide; DALIAN BLUESCITECH TECHNOLOGY RESEARCH AND DEVELOPMENT CO., LTD.) | Solution A after heat treatment (pH 2.5) | 66.53 | −15.33 | −23.03 | 27.67 | 6.38 |
| | | Non-heat treated solution B (pH 6.0) | 66.75 | −19.75 | −27.62 | 33.95 | — |
| Comparative Example 7-4 | Fish collagen peptide (Fish collagen tripeptide; WUHAN TALLYHO BIOLOGICAL PRODUCT CO., LTD.) | Solution A after heat treatment (pH 2.5) | 58.32 | −14.24 | −31.41 | 34.48 | 8.04 |
| | | Non-heat treated solution B (pH 6.0) | 62.10 | −16.52 | −30.00 | 34.25 | — |
| Comparative Example 7-5 | Histidine | Solution A after heat treatment (pH 2.5) | 68.18 | −13.24 | −26.92 | 30.00 | 3.20 |
| | | Non-heat treated solution B (pH 6.0) | 69.67 | −15.19 | −27.23 | 31.18 | — |

[#]The $\Delta E^*_{ab}$ value represents the value of the color difference relative to non-heat treated solution B as the reference.

The invention claimed is:

1. A gardenia blue pigment, wherein, when prepared as a solution with a color value $E^{10\%}_{1\,cm}$ of 0.1 by diluting with water, the gardenia blue pigment has an L* value of 66 or more and an a* value of −24 or less in the Lab color space.

2. The gardenia blue pigment according to claim 1, wherein, when prepared as a solution with a color value $E^{10\%}_{1\,cm}$ of 0.1 by diluting with water, the gardenia blue pigment has a b* value of −30 or more in the Lab color space.

3. The gardenia blue pigment according to claim 1, wherein, when the gardenia blue pigment is subjected to operations as set forth in (1) to (3) below, a color difference $\Delta E^*_{ab}$ between solution A heat-treated at 90° C. for 15 minutes and solution B not heat-treated is 3.5 or less, and solution A heat-treated at 90° C. for 15 minutes has an L* value of 64 or more, an a* value of −14 or less, and a b* value of −31 or more:

the operations comprising:

(1) a preparation step, wherein
the gardenia blue pigment is diluted with 0.1 M citrate buffer at pH 2.5 to prepare solution A with a color value $E^{10\%}_{1\,cm}$ of 0.1; separately, the gardenia blue pigment is diluted with 0.1 M citrate buffer at pH 6.0 to prepare solution B with a color value $E^{10\%}_{1\,cm}$ of 0.1;

(2) a heat-treatment of the solutions step wherein solution A is heat-treated at 90° C. for 15 minutes; solution B is not heat-treated;

(3) a measurement of color tone step wherein
for solution A heat-treated at 90° C. for 15 minutes and solution B not heat-treated, the L* value, the a* value, and the b* value in the Lab color space are measured.

4. The gardenia blue pigment according to claim 1, wherein a maximum absorption wavelength is present in a range of 604 nm or more.

5. A food or beverage product colored with the gardenia blue pigment according to claim 1.

* * * * *